United States Patent
Bowman et al.

(10) Patent No.: US 8,920,921 B2
(45) Date of Patent: Dec. 30, 2014

(54) TERPOLYMER BLENDS AND THEIR USE AS PRESSURE-SENSITIVE ADHESIVES

(75) Inventors: Howard Bowman, Birmingham, AL (US); Bruce W. Hudson, Pleasant Grove, AL (US)

(73) Assignee: Surmodics Pharmaceuticals, Inc., Birmingham, AL (US)

(*) Notice: Subject to any disclaimer, the term of this patent is extended or adjusted under 35 U.S.C. 154(b) by 573 days.

(21) Appl. No.: 13/221,415

(22) Filed: Aug. 30, 2011

(65) Prior Publication Data
US 2012/0077028 A1 Mar. 29, 2012

Related U.S. Application Data

(60) Provisional application No. 61/378,134, filed on Aug. 30, 2010, provisional application No. 61/378,212, filed on Aug. 30, 2010, provisional application No. 61/380,937, filed on Sep. 8, 2010, provisional application No. 61/378,235, filed on Aug. 30, 2010.

(51) Int. Cl.
| | |
|---|---|
| *C08G 63/08* | (2006.01) |
| *C09J 7/02* | (2006.01) |
| *A61L 15/26* | (2006.01) |
| *C09J 167/04* | (2006.01) |
| *C09J 7/00* | (2006.01) |
| *A61L 15/58* | (2006.01) |
| *A61L 24/04* | (2006.01) |
| *C08L 67/04* | (2006.01) |

(52) U.S. Cl.
CPC .............. *C08G 63/08* (2013.01); *C09J 7/0207* (2013.01); *A61L 15/26* (2013.01); *C09J 7/0285* (2013.01); *C09J 167/04* (2013.01); *C09J 2467/006* (2013.01); *C09J 7/00* (2013.01); *A61L 15/58* (2013.01); *C08L 67/04* (2013.01); *A61L 24/046* (2013.01); *C09J 2467/00* (2013.01)
USPC .......................... 428/352; 428/500; 525/450

(58) Field of Classification Search
None
See application file for complete search history.

(56) References Cited

U.S. PATENT DOCUMENTS

| | | | |
|---|---|---|---|
| 4,020,558 A | 5/1977 | Cournut et al. | |
| 4,241,489 A | 12/1980 | Manning | |

(Continued)

FOREIGN PATENT DOCUMENTS

| | | |
|---|---|---|
| CA | 2705520 | 5/2009 |
| EP | 0306212 | 3/1989 |

(Continued)

OTHER PUBLICATIONS

Beletsi et al. (Effect of preparative variables on the properties of poly(dl-lactide-co-glycolide)-methoxypoly(ethyleneglycol) copolymers related to their application in controlled drug delivery, Int. J. of Pharm. 182 (1999) 187-197).*

(Continued)

*Primary Examiner* — Mark Ruthkosky
*Assistant Examiner* — Alexandre Ferre
(74) *Attorney, Agent, or Firm* — Pauly, DeVries Smith & Deffner, LLC

(57) ABSTRACT

Disclosed herein are blends prepared from polyester terpolymers that function as pressure-sensitive adhesives. The disclosed articles comprise the terpolymer blends adhered to a release liner. The disclosed implant devices comprise the pressure-sensitive adhesive blend adhered to a surface thereof. The pressure-sensitive adhesive blend can promote adhesion of the implant device to a location in a subject.

22 Claims, 2 Drawing Sheets

(56) References Cited

U.S. PATENT DOCUMENTS

| | | | |
|---|---|---|---|
| 4,704,692 A | 11/1987 | Ladner | |
| 4,804,691 A | 2/1989 | English et al. | |
| 4,874,612 A | 10/1989 | Deasy | |
| 4,892,736 A | 1/1990 | Goodson | |
| 4,898,734 A | 2/1990 | Mathiowitz et al. | |
| 5,004,602 A | 4/1991 | Hutchinson | |
| 5,076,807 A | 12/1991 | Bezwada et al. | |
| 5,278,201 A | 1/1994 | Dunn et al. | |
| 5,281,354 A | 1/1994 | Faber | |
| 5,407,609 A | 4/1995 | Tice et al. | |
| 5,468,253 A | 11/1995 | Bezwada et al. | |
| 5,514,378 A | 5/1996 | Mikos et al. | |
| 5,558,877 A | 9/1996 | Matlin et al. | |
| 5,568,866 A | 10/1996 | Grosskopf et al. | |
| 5,599,552 A | 2/1997 | Dunn et al. | |
| 5,599,852 A | 2/1997 | Scopelianos et al. | |
| 5,702,717 A * | 12/1997 | Cha et al. | 424/425 |
| 5,705,716 A | 1/1998 | Li | |
| 5,739,176 A | 4/1998 | Dunn et al. | |
| 5,759,563 A | 6/1998 | Yewey et al. | |
| 5,876,452 A * | 3/1999 | Athanasiou et al. | 623/23.72 |
| 5,945,115 A | 8/1999 | Dunn et al. | |
| 6,006,122 A | 12/1999 | Smits | |
| 6,086,526 A | 7/2000 | Francischelli | |
| 6,126,919 A | 10/2000 | Stefely et al. | |
| 6,130,200 A | 10/2000 | Brodbeck et al. | |
| 6,331,311 B1 | 12/2001 | Brodbeck et al. | |
| 6,338,859 B1 | 1/2002 | Leroux et al. | |
| 6,413,536 B1 | 7/2002 | Gibson et al. | |
| 6,432,438 B1 | 8/2002 | Shukla | |
| 6,467,621 B1 | 10/2002 | Ishida | |
| 6,468,961 B1 | 10/2002 | Brodbeck et al. | |
| 6,469,132 B1 | 10/2002 | Eisenberg et al. | |
| 6,471,987 B1 | 10/2002 | McBride-Sakal et al. | |
| 6,477,428 B1 | 11/2002 | Skinner et al. | |
| RE37,950 E | 12/2002 | Dunn et al. | |
| 6,673,767 B1 | 1/2004 | Brodbeck et al. | |
| 6,747,121 B2 | 6/2004 | Gogolewski | |
| 6,845,352 B1 | 1/2005 | Wang | |
| 6,846,795 B2 | 1/2005 | Lant et al. | |
| 6,849,426 B2 | 2/2005 | Chen et al. | |
| 6,852,816 B2 | 2/2005 | Lewis et al. | |
| 6,923,985 B2 | 8/2005 | Peterson et al. | |
| 6,939,569 B1 | 9/2005 | Green et al. | |
| 7,008,979 B2 | 3/2006 | Schottman et al. | |
| 7,022,343 B2 | 4/2006 | Philbrook et al. | |
| 7,053,209 B1 | 5/2006 | Gibson et al. | |
| 7,074,426 B2 | 7/2006 | Kochinke | |
| 7,122,205 B2 | 10/2006 | Peterson et al. | |
| 7,128,927 B1 | 10/2006 | Dunn | |
| 7,153,520 B2 | 12/2006 | Seo et al. | |
| 7,299,905 B2 | 11/2007 | Yamaguchi et al. | |
| 7,368,126 B2 * | 5/2008 | Chen et al. | 424/426 |
| 7,798,954 B2 | 9/2010 | Birk et al. | |
| 8,025,635 B2 | 9/2011 | Eaton et al. | |
| 8,492,512 B2 | 7/2013 | Raiche et al. | |
| 2001/0000142 A1 | 4/2001 | Santos et al. | |
| 2002/0150622 A1 | 10/2002 | Philbrook et al. | |
| 2003/0114637 A1 | 6/2003 | Gogolewski | |
| 2003/0185872 A1 | 10/2003 | Kochinke | |
| 2003/0203991 A1 | 10/2003 | Schottman et al. | |
| 2004/0006199 A1 | 1/2004 | Newman, Jr. et al. | |
| 2004/0037885 A1 | 2/2004 | Seo et al. | |
| 2004/0052859 A1 | 3/2004 | Wu et al. | |
| 2004/0146546 A1 | 7/2004 | Gravett et al. | |
| 2005/0079202 A1 | 4/2005 | Chen et al. | |
| 2005/0129732 A1 | 6/2005 | Rubsamen | |
| 2005/0267543 A1 | 12/2005 | Heruth et al. | |
| 2006/0147491 A1 | 7/2006 | Dewitt et al. | |
| 2006/0212113 A1 | 9/2006 | Shaolian et al. | |
| 2007/0005094 A1 | 1/2007 | Eaton et al. | |
| 2007/0184084 A1 | 8/2007 | Chen et al. | |
| 2007/0190154 A1 | 8/2007 | Zeigerson | |
| 2007/0202145 A1 | 8/2007 | Ghabrial et al. | |
| 2007/0207189 A1 | 9/2007 | Belcheva et al. | |
| 2007/0265645 A1 | 11/2007 | Birk et al. | |
| 2008/0118541 A1 | 5/2008 | Pacetti | |
| 2008/0125728 A1 | 5/2008 | Bischoff et al. | |
| 2008/0208323 A1 | 8/2008 | El-Kurdi et al. | |
| 2008/0260796 A1 | 10/2008 | Bischoff et al. | |
| 2009/0004243 A1 | 1/2009 | Pacetti et al. | |
| 2009/0124535 A1 * | 5/2009 | Markland et al. | 514/2 |
| 2009/0198197 A1 | 8/2009 | Bischoff et al. | |
| 2009/0306120 A1 * | 12/2009 | Lim et al. | 514/291 |
| 2010/0098744 A1 | 4/2010 | Ferris et al. | |
| 2010/0158969 A1 | 6/2010 | Tice | |
| 2010/0158970 A1 | 6/2010 | Tipton et al. | |
| 2010/0158978 A1 | 6/2010 | Markland | |
| 2010/0160891 A1 | 6/2010 | Tipton et al. | |
| 2010/0160892 A1 | 6/2010 | Tice | |
| 2010/0168807 A1 | 7/2010 | Burton et al. | |
| 2010/0198278 A1 | 8/2010 | Cobian et al. | |
| 2010/0203100 A1 | 8/2010 | Cobian et al. | |
| 2010/0247596 A1 | 9/2010 | Bischoff | |
| 2011/0098813 A1 | 4/2011 | Gibson | |
| 2011/0129422 A1 | 6/2011 | Markland et al. | |
| 2011/0159072 A1 | 6/2011 | Missling et al. | |
| 2012/0077887 A1 | 3/2012 | Bowman et al. | |
| 2012/0077954 A1 | 3/2012 | Raiche et al. | |
| 2012/0078155 A1 | 3/2012 | Bowman et al. | |

FOREIGN PATENT DOCUMENTS

| | | | |
|---|---|---|---|
| EP | 1917971 | 5/2008 | |
| EP | 2050474 | 4/2009 | |
| EP | 2123312 | 11/2009 | |
| EP | 2219620 | 8/2010 | |
| EP | 2611868 | 7/2013 | |
| JP | 08206191 | 8/1996 | |
| JP | 11181077 | 7/1999 | |
| JP | 11343228 | 12/1999 | |
| JP | 2000159865 | 6/2000 | |
| JP | 2000508931 | 7/2000 | |
| JP | 2004514734 | 5/2004 | |
| JP | 2012513473 | 6/2012 | |
| JP | 2013543521 | 12/2013 | |
| WO | 9738676 | 10/1997 | |
| WO | WO 9738676 A1 * | 10/1997 | A61K 9/10 |
| WO | 0245689 | 6/2002 | |
| WO | 2006124021 | 11/2006 | |
| WO | 2009064442 | 5/2009 | |
| WO | 2010075298 | 7/2010 | |
| WO | 2012030819 | 3/2012 | |
| WO | 2012030821 | 3/2012 | |
| WO | 2012030822 | 3/2012 | |
| WO | 2012030823 | 3/2012 | |

OTHER PUBLICATIONS

Beletsi, A et al., "Effect of Preparative Variables on the Properties of poly(dl-lactide-co-glycolide)—methoxypoly (ethyleneglycol) Copolymers Related to Their Applicaiton in Controlled Drug Delivery", International Journal of Pharmaceuticals, 182 (1999) pp. 187-197.

Bodansky, M. et al., "Utilization of Poly Glycerol Esters", Ed. Principles of Peptide Synthesis, Springer-Verlag, Inc, N.Y., 1993, (p. 1938-1942).

Final Office Action, for U.S. Appl. No. 12/644,097, mailed Feb. 28, 2013 (28 pages).

Final Office Action, for Japanese Patent Application No. 2010-534036, mailed Nov. 6, 2013 (4 pages) with English translation.

Final Office Action, for U.S. Appl. No. 12/269,135, mailed Mar. 21, 2014 (29 pages).

Final Office Action, for U.S. Appl. No. 12/644,097, mailed Apr. 9, 2014 (20 pages).

Final Office Action, for U.S. Appl. No. 13/221,389, mailed Sep. 10, 2013 (38 pages).

Final Office Action, from U.S. Appl. No. 12/643,558, mailed May 10, 2013, 15 pages.

Final Office Action, mailed Apr. 9, 2012 in co-pending U.S. Appl. No. 12/644,097, "Bioactive Terpolymer Compositions and Methods of Making and Using Same," (16 pages).

(56) References Cited

OTHER PUBLICATIONS

"Final Office Action", mailed Dec. 2, 2011 in co-pending U.S. Appl. No. 12/643,558, "Flexible Implantable Composites and Implants Comprising Same," (19 Pages).
"Final Office Action", mailed Jun. 3, 2011 in co pending U.S. Appl. No. 12/269,135, "Viscous Terpolymers as Drug Delivery Platform" (24 pages).
"Final Office Action", mailed May 18, 2012 in U.S. Appl. No. 12/643,546, "Elastic Implantable Composites and Implants Comprising Same," (11 pages).
"Final Office Action", mailed Oct. 28, 2011 in co-pending U.S. Appl. No. 12/643,571, "Implantable Suction Cup Composites and Implants Comprising Same," (22 pages).
"Final Office Action", mailed Sep. 27, 2012 in U.S. Appl. No. 12/643,580, "Bioactive Spray Coating Compositions and Methods of Making and Uses Thereof," (8 pages).
Gollwitzer, et al., "Antibacterial poly(D,L-lactic acid) coating of medical implants using a biodegradable drug delivery technology", Journal of Antimicrobial Chemotherapy, 2003, pp. 585-591.
Grant,, "Synthetic Peptides: A User Guide", W.H. Freemean and Co., N.Y., 1992, (25 pgs).
Harlow, Ed, "Antibodies, a Laboratory Manual", Cold Spring Harbor Publications, N.Y., 1988, (4 pages).
Hong, et al., "Generating Elastic, Biodegradable Poolyurethane/Poly(lactide-co-glycolide) Fibrous Sheets with Controlled Antibiotic Release via Two-Stream Electrospinning", Biomacromolecules, 9, 2008, pp. 1200-1207.
"International Preliminary Report on Patentability", from International Application No. PCT/US2008/012755, mailed May 18, 2010, (5 pages).
"International Preliminary Report on Patentability", from International Application No. PCTUS2009069024, mailed Jul. 7, 2011 (13 pages).
International Preliminary Report on Patentability, from PCT Application No. PCT/US2011/049730, mailed Mar. 14, 2013, 8 pages.
International Preliminary Report on Patentability, from PCT Application No. PCT/US2011/049731, mailed Mar. 14, 2013, 6 pages.
International Preliminary Report on Patentability, from PCT Application No. PCT/US2011/049735, mailed Mar. 14, 2013, 10 pages.
"International Preliminary Report on Patentability", from PCT/US2011/049726, mailed Mar. 14, 2013, 8 pages.
"International Search Report and Written Opinion", from International Application No. PCT/US2008/012755, mailed Jan. 29, 2009, (6 pages).
"International Search Report and Written Opinion", from International Application No. PCT/US2009/069024, mailed Nov. 26, 2010, (16 pages).
"International Search Report and Written Opinion", from International Application No. PCT/US2011/049726, mailed Nov. 18, 2011, pp. 1-11.
"International Search Report and Written Opinion", from International Application No. PCT/US2011/049730, mailed Nov. 18, 2011, pp. 1-20.
"International Search Report and Written Opinion", from International Application No. PCT/US2011/049731, mailed Feb. 14, 2012, pp. 1-9.
"International Search Report and Written Opinion", from International Application No. PCT/US2011/049735, mailed Nov. 18, 2011, pp. 1-15.
Kastin, Abba J., "Handbook of Biologically Active Peptides", Academic Press, 2006, (6 pages).
Kobayashi, et al., "Bioconjugate Chem", vol. 12, pp. 100-107, (2001).
Kobayashi, et al., "Mag Res in Medicine", vol. 46, pp. 579-585, (2001).
Kulkarni, et al., "Poly(lactic acid) for Surgical Implants", Technical Rep. 6608, Walter Reed Army Medical Center, Washington, D.C., 1966.
Letsinger, et al., "Proceedings of the Naitonal Academy of Sciences", vol. 86, pp. 6553-6556, 1989.

Miller, et al., "Degradation Ratesof Oral Resorbable Implants (polylactates and polyglycolates): Rate Modification iwth Changes in PLA/PGA Copolymer Ratios", J. Biomed. Matr. Res. 11, 1977, pp. 711-719, (12 pages).
Nagy, et al., "Immunomodulation by tamoxifen and pergolide", Immunopharmacology, 12(2), Oct. 1986, pp. 1-2 (abstract only, pp. 1,2).
Nielson, Peter E. et al., "Bioconjug. Chem.", vol. 5, pp. 3-7, 1994.
"Non-Final Office Action", mailed Aug. 3, 2011 in co-pending U.S. Appl. No. 12/643,558, "Flexible Implantable Composites and Implants Comprising Same," (27 pages).
"Non-Final Office Action", mailed Mar. 16, 2012 in co-pending U.S. Appl. No. 12/643,580, "Bioactive Spray Coating Compositions and Methods of Making and Uses Thereof," (31 pages).
"Non-Final Office Action", mailed Oct. 11, 2011 in co-pending U.S. Appl. No. 12/644,097, "Bioactive Terpolymer Compositions and Methods of Making and Using Same" (48 pages).
"Non-Final Office Action", for U.S. Appl. No. 12/269,135, mailed Sep. 23, 2013 (32 pages).
"Non-Final Office Action", for U.S. Appl. No. 12/644,097, mailed Jul. 19, 2013 (37 pages).
"Non-Final Office Action", for U.S. Appl. No. 12/643,558, mailed Apr. 1, 2014 (26 pages).
"Non-Final Office Action", from U.S. Appl. No. 12/643,546, mailed Jun. 19, 2013, 12 pages.
"Non-Final Office Action", from U.S. Appl. No. 13/221,389, mailed Apr. 9, 2013, 17 pages.
"Non-Final Office Action", mailed Jan. 7, 2013 in co-pending U.S. Appl. No. 12/643,558, "Flexible Implantable Composites and Implants Comprising Same," (15 pages)., 15.
"Non-Final Office Action", mailed Dec. 15, 2011 in co-pending U.S. Appl. No. 12/643,546, "Elastic Implantable Composites and Implants Comprising Same," (32 pages).
"Non-Final Office Action", mailed Jul. 5, 2012 in co-pending U.S. Appl. No. 13/221,429, "Process for Reducing Moisture in a Biodegradable Implant Device" (6 pages).
"Non-Final Office Action", mailed Jun. 8, 2011, in co-pending U.S. Appl. No. 12/643,571, (11 pages).
"Non-Final Office Action", mailed Oct. 8, 2010 in U.S. Appl. No. 12/269,135, "Viscous Terpolymers as a Drug Delivery Platform," (22 pages).
"Non-Final Office Action", mailed Sep. 20, 2012 in Application U.S. Appl. No. 12/644,097, "Bioactive Terpolymer Compositions and Methods of Making and Using Same," (38 pages).
"Notice of Allowance", for U.S. Appl. No. 12/643,546, mailed Feb. 21, 2014 (8 pages).
"Notice of Allowance", from U.S. Appl. No. 13/221,429, mailed Mar. 22, 2013, 20 pgs.
"Notice of Allowance", mailed Oct. 23, 2012 in U.S. Appl. No. 13/221,429, "Process for Reducing Moisture in a Biodegradable Implant Device," (5 pages).
Office Action, from JP Application No. 2010-534036, mailed Jun. 11, 2013, 7 pages.
Mundargi, Raghavendra C. et al., "Development and evaluation of novel biodegradable microspheres based on poly(D,L-Lactide-co-glycolide) and poly(e-caprolactone) for controlled delivery of doxycyline in the treatment of human periodontal pocket: In vitro and in vivo studies", Journal of Controlled Release 119, 2007, pp. 59-68.
Remington "The Science and Practice of Pharmacy", 21st Ed., Lippincott Williams & Wilkins, Philadelphia, PA, 2005, (14 pages).
Response to Final Office Action, for U.S. Appl. No. 12/643,558, mailed Aug. 2, 2013 and filed with the USPTO Aug. 2, 2013 (7 pages).
"Response to Final Office Action", for U.S. Appl. No. 13/221,389, mailed Sep. 10, 2013 and filed with the USPTO Jan. 10, 2014 (9 pages).
"Response to Final Office Action", mailed Aug. 20, 2012 in co-pending U.S. Appl. No. 12/643,546 9 pages.
"Response to Final Office Action", mailed Dec. 27, 2012 in U.S. Appl. No. 12/643,580, "Bioactive Spray Coating Compositions and Methods of Making and Uses Thereof", 5 pages.

(56) References Cited

OTHER PUBLICATIONS

"Response to Final Office Action", mailed Feb. 28, 2013, in co-pending U.S. Appl. No. 12/644,097, filed with USPTO May 24, 2013, (12 pages).
"Response to Final Office Action", mailed Jan. 26, 2012 in co-pending U.S. Appl. No. 12/643,571 11 pages.
"Response to Final Office Action", mailed Jul. 9, 2012 in U.S. Appl. No. 12/644,097, "Bioactive Terpolymer Compositions and Methods of Making an Dusing Same", (10 pages).
"Response to Final Office Action", mailed Mar. 2, 2012 in co-pending U.S. Appl. No. 12/643,558 10 pages.
"Response to Final Office Action", mailed Sep. 6, 2011 in U.S. Appl. No. 12/269,135, "Viscous Terpolymers as Drug Delivery Platform", 10 pages.
"Response to Non Final Office Action", mailed Jan. 3, 2012 in U.S. Appl. No. 12/644,097, "Bioactive Terpolymer Compositions and Methods of Making and Using Same", (8 pages).
"Response to Non Final Office Action", mailed Oct. 31, 2011 in U.S. Appl. No. 12/643,558, "Flexible Implantable Composites and Implants Comprising Same", (8 pages).
"Response to Non-Final Office Action", for U.S. Appl. No. 12/269,135, mailed Jan. 23, 2014 (10 pages).
"Resposne to Non-Final Office Action", for U.S. Appl. No. 12/643,546, mailed Jun. 19, 2013 and filed with the USPTO Dec. 19, 2013 (7 pages).
"Response to Non-Final Office Action", for U.S. Appl. No. 12/644,097, mailed Jul. 19, 2013 and filed with the USPTO Dec. 19, 2013 (7 pages).
"Response to Non-Final Office Action", mailed Apr. 9, 2013, in co-pending U.S. Appl. No. 13/221,389, filed with USPTO Jul. 2, 2013 (9 pages).
"Response to Non-Final Office Action", mailed Jan. 7, 2013, in co-pending U.S. Appl. No. 12/643,558, filed with USPTO Apr. 8, 2013, (9 pages).
"Response to Non-Final Office Action", mailed Jun. 14, 2012 in co-pending U.S. Appl. No. 12/643,580 6 pages.
"Response to Non-Final Office Action", mailed Jun. 8, 2011, in co-pending U.S. Appl. No. 12/643,571, filed with USPTO Aug. 17, 2011, (10 pages).
"Response to Non-Final Office Action", mailed Mar. 14, 2012 in co-pending U.S. Appl. No. 12/643,546 8 pages.
"Response to Non-Final Office Action", mailed Oct. 2, 2012 in co-pending U.S. Appl. No. 13/221,429 5 pages.
"Response to Non-Final Office Action", mailed Oct. 8, 2010 in U.S. Appl. No. 12/269,135, filed with USPTO Apr. 8, 2011, (7 pages).
"Response to Non-Final Office Action", mailed Sep. 20, 2012, in co-pending U.S. Appl. No. 12/644,097, filed with USPTO Jan. 18, 2013, (10 pages).
"Response to Restriction Requirement", mailed Feb. 6, 2012 in co-pending U.S. Appl. No. 12/643,580 5 pages.
"Restriction Requirement", mailed Jan. 6, 2012 in co-pending U.S. Appl. No. 12/643,580, "Bioactive Spray Coating Compositions and Methods of Making and Uses Thereof," (6 pages).
Sakkas, P, "The Future: Towards Long Acting Atypical Anti-Psychosis", Annals of General Hosipital Psychiatry, Oral Presentation, Dec. 23, 2002, 1 pg.
Sawhney,, "Rapidly degraded terpolymers of dl-lactide, glycolide, and [epsilon]—caprolactone with increased hydrophilicity by copolymerization with ployethers", Journal of Biomedical Materials Research, Wiley, New York, NY, US vol. 24, No. 10, Oct. 1, 1990, pp. 1397-1411.
SRISA-ARD, Mangkorn et al., "Synthesis and characterization of a random terpolymer of L-lactide, e-caprolactone and glycolide", Society of Chemical Industry, Polymer International, vol. 50, Issue 8 (Jul. 20, 2001) pp. 891-896.
Stolnik, et al., "Polylactide—Poly(ethylene glycol) micellar-like Particles as Potential Drug Carriers: Production, Colloidal Properties and Biological Performance", J. Drug Targeting, 2001 (18 pages).
Lu, Chengfei et al., "Synthesis and Aggregation Behavior of four types of different Shaped PCL-PEG Block Copolymers", Polymer International, vol. 55, 2006, pp. 694-700.
"Non-Final Office Action", for U.S. Appl. No. 13/221,389, mailed Aug. 25, 2014 (22 pages).
"Response to Non-Final Office Action", for U.S. Appl. No. 12/643,580, filed with the USPTO Nov. 20, 2014 (7 pages).
"Response to Non-Final Office Action", for U.S. Appl. No. 13/221,464, filed with the USPTO Sep. 9, 2014 (18 pages).

* cited by examiner

US 8,920,921 B2

TERPOLYMER BLENDS AND THEIR USE AS PRESSURE-SENSITIVE ADHESIVES

This application claims priority to U.S. Provisional Application No. 61/378,134, filed Aug. 30, 2010, U.S. Provisional Application No. 61/378,212, filed Aug. 30, 2010, U.S. Provisional Application No. 61/378,235, filed Aug. 30, 2010, and U.S. Provisional Application No. 61/380,937, filed Sep. 8, 2010, the content of all of which is herein incorporated by reference in its entirety.

BACKGROUND

A pressure-sensitive adhesive (PSA) can be a viscoelastic (viscous and elastic) substance capable of forming a bond with an adherent upon the application of pressure. A PSA can thus be soft enough to flow, or wet, but hard enough to resist flow when stress is applied. Pressure-sensitive adhesives can provide advantages over other adhesives inasmuch as they do not require cure time and other processing steps often required with the use of other adhesives.

Commercially available PSAs often include polymers such as natural rubber, polynitrile, acrylic, isobutylene, silicone and styrene. Typically, these PSAs are made from petroleum sources, have attractive fiber and structural properties, are low in cost and are easily processed. One disadvantage with many PSAs, however, is that they do not degrade into components that can be metabolized by microbial populations or in vivo. Such PSAs are thus limited in their use in biomedical applications and other applications for which a biocompatible or biodegradable PSA would be useful. A need therefore exists for new biocompatible and biodegradable PSAs.

SUMMARY

In one aspect, the blend described herein comprises: (a) a first poly(D,L-lactide-co-glycol lactide-co-ε-caprolactone) having a molecular weight ($M_w$) of from 75,000 to 250,000 Daltons and a polydispersity index (PDI) of less than 2.0, and (b) a second poly(D,L-lactide-co-glycolide-co-ε-caprolactone) having a molecular weight ($M_w$) of 130,000 Daltons or less and a polydispersity index (PDI) of less than 2.0; wherein the second poly(D,L-lactide-co-glycolide-co-ε-caprolactone) has a molecular weight ($M_w$) that is less than the first poly(D,L-lactide-co-glycolide-co-ε-caprolactone); and wherein the weight ratio of the first poly(D,L-lactide-co-glycolide-co-ε-caprolactone) to the second poly(D,L-lactide-co-glycolide-co-ε-caprolactone) is from about 90:10 to about 60:40.

In another aspect, the blend comprises: (a) a poly(D,L-lactide-co-glycolide-co-ε-caprolactone) having a molecular weight of from 75,000 to 250,000 Daltons and a polydispersity index (PDI) of less than 2.0, and (b) a poly(D,L-lactide-co-glycolide-co-mPEG) having a molecular weight ($M_w$) of less than 25,000 Daltons and a polydispersity index (PDI) of less than 2.0; wherein the poly(D,L-lactide-co-glycolide-co-mPEG) has a molecular weight ($M_w$) that is less than the poly(D,L-lactide-co-glycolide-co-ε-caprolactone); and wherein the weight ratio of the poly(D,L-lactide-co-glycolide-co-ε-caprolactone) to the poly(D,L-lactide-co-glycolide-co-mPEG) is from about 95:5 to about 75:25.

The disclosed article comprises a pressure-sensitive adhesive (PSA) having a first adhesive surface and an opposing second adhesive surface, the pressure-sensitive adhesive (PSA) comprising a disclosed blend; and a release liner having a surface thereof adhered to the first adhesive surface of the pressure-sensitive adhesive.

The disclosed implant device comprises a substrate having a disclosed adhered to a surface thereof.

DETAILED DESCRIPTION

Figure 1:
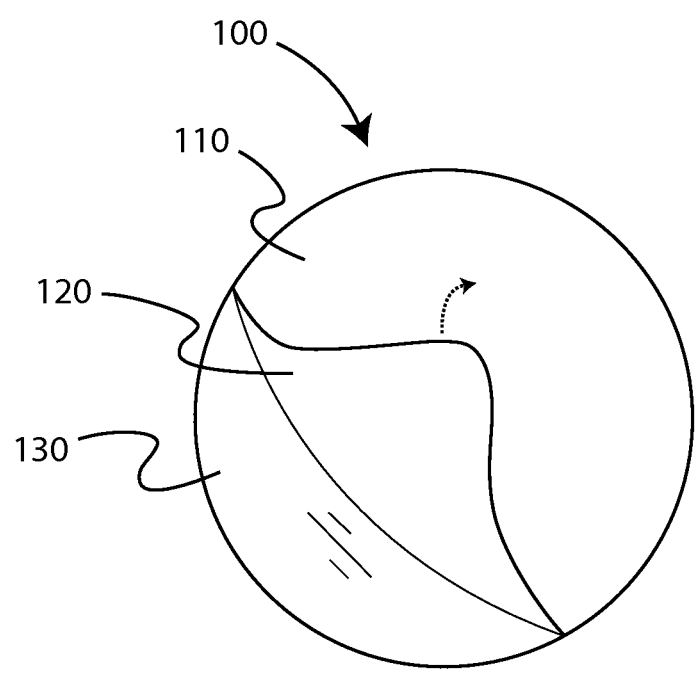
FIG. 1 is a drawing of an article comprising a pressure-sensitive adhesive blend adhered to a release liner.

In this specification and in the claims that follow, reference will be made to a number of terms that have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

Singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Molecular weight" or "$M_w$," as used herein, refers to the weight average molecular weight as determined by gel-permeation chromatography.

"Polydispersity index," or "PDI," as used herein, refers to the value obtained by dividing $M_w$ by $M_n$ (number average molecular weight). Both $M_w$ and $M_n$ are determined by gel-permeation chromatography.

"Glass transition temperature" or "$T_g$" refers to the glass transition temperature as determined by differential scanning calorimetry (DSC). DSC defines the glass transition as a change in the heat capacity as the polymer goes from the glass state to the rubber state. This is a second order endothermic transition (requires heat to go through the transition), and thus the transition appears as a step transition, rather than a peak as would be expected with a first order phase transition.

"Mole ratio," "molar ratio," and "mole percent," as used herein refer to the molar percentages of each polymer in the blend. Molar percentages are determined by $^1H$ NMR analysis of each individual terpolymer in the terpolymer blend.

The term "implant device" refers to any formulation or article that is greater than 1 mm in length in at least one dimension of the device. The device can comprise a disclosed composition. In a further aspect, the device has one dimension that is from 1 mm to 50 mm, 1.2 mm to 45 mm, 1.4 mm to 42 mm, 1.6 mm to 40 mm, 1.8 mm to 38 mm, or 2.0 mm to 36 mm, 5.0 mm to 33 mm, or 10 mm to 30 mm. In a further aspect, the device has one dimension that is greater than 3 cm, even up to or greater than 10 cm, 20 cm, or even 30 cm.

"Biodegradable" refers to materials that will erode to soluble species or that will degrade under physiologic conditions to smaller units or chemical species that are, themselves, non-toxic (biocompatible) to the subject and capable of being metabolized, eliminated, or excreted by the subject.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. Bioactive agents also include those substances which affect the structure or function of a subject, or a pro-drug, which becomes bioactive or more bioactive after it has been placed in a predetermined physiological environment.

"mPEG" refers to methoxypoly(ethylene glycol).

In one aspect, the blends function as pressure-sensitive adhesives. The pressure sensitive adhesive can be part of an article comprising a release liner adhered to a surface of the pressure-sensitive adhesive blend. The blends can also be applied to an implant device. The implant devices comprising the pressure-sensitive adhesive blends can be implanted in a subject and adhered (through the blend) to a particular location in the subject. The blends generally comprise linear polyester terpolymers that can remain tacky over extended periods of time and can adhere to a solid surface upon the application of light pressure, without the aid of a solvent. The blends can exist in a variety of physical states, including a low viscosity liquid, viscous paste, film, semisolid, or solid.

In one aspect, the blend comprises (a) a first poly(D,L-lactide-co-glycolide-co-ϵ-caprolactone) having a molecular weight (Mw) of from 75,000 to 250,000 Daltons and a polydispersity index (PDI) of less than 2.0, and (b) a second poly(D,L-lactide-co-glycolide-co-ϵ-caprolactone) having a molecular weight (Mw) of 130,000 Daltons or less and a polydispersity index (PDI) of less than 2.0.

The first poly(D,L-lactide-co-glycolide-co-ϵ-caprolactone) can be elastomeric or viscoelastic, and the second poly(D,L-lactide-co-glycolide-co-ϵ-caprolactone) can be tacky or sticky. The blended composition of the first and second polymer thus functions as a pressure-sensitive adhesive, which can adhere to a variety of substrates with the application of light pressure.

The first poly(D,L-lactide-co-glycolide-co-ϵ-caprolactone) has a molecular weight ($M_w$) of from 75,000 to 250,000 Daltons, and in some embodiments, from 100,000 to 130,000 Daltons. For example, the first poly(D,L-lactide-co-glycolide-co-ϵ-caprolactone) can have a molecular weight ($M_w$) of 100,000, 110,000, 112,000, 113,000, 115,000, 119,000, or 125,000 Daltons. The second poly(D,L-lactide-co-glycolide-co-ϵ-caprolactone) can have a molecular weight of 130,000 Daltons or less, and in some embodiments, from 60,000 to 130,000 Daltons. For example, the second poly(D,L-lactide-co-glycolide-co-ϵ-caprolactone) can have a molecular weight ($M_w$) of 60,000, 70,000, 80,000, 90,000, 100,000, or 120,000 Daltons.

The second poly(D,L-lactide-co-glycolide-co-ϵ-caprolactone) has a molecular weight (Mw) that can be less than the first poly(D,L-lactide-co-glycolide-co-ϵ-caprolactone). The second poly(D,L-lactide-co-glycolide-co-ϵ-caprolactone) can have a molecular weight ($M_w$) that can be from 10% to 90% of the molecular weight of the second poly(D,L-lactide-co-glycolide-co-ϵ-caprolactone). For example, the second poly(D,L-lactide-co-glycolide-co-ϵ-caprolactone) can have a molecular weight ($M_w$) that can be 10%, 20%, 30%, 40%, 50%, 60%, 70%, 80%, or 90% of the molecular weight ($M_w$) value of the first poly(D,L-lactide-co-glycolide-co-ϵ-caprolactone).

The first and second poly(D,L-lactide-co-glycolide-co-ϵ-caprolactone)s each have a polydispersity index (PDI) that can be less than about 2.0, and from about 1.5 to about 1.8. The PDI of the first and second polymer can be the same or different.

The first and second poly(D,L-lactide-co-glycolide-co-ϵ-caprolactone)s both generally have a glass transition temperature ($T_g$) of 0° C. or less, such as from about −20° C. to about 0° C. For example, the first and second poly(D,L-lactide-co-glycolide-co-ϵ-caprolactone)s can each have a glass transition temperature ($T_g$) that can be the same or different, of 0, −5, −8, −9, −10, −12, −15, or −20° C.

The weight ratio of the first poly(D,L-lactide-co-glycolide-co-ϵ-caprolactone) to the second poly(D,L-lactide-co-glycolide-co-ϵ-caprolactone) can range from about 90:10 to about 60:40, for example, 90:10, 80:20, 70:30, or 60:40.

The first and second poly(D,L-lactide-co-glycolide-co-ϵ-caprolactone)s can have various mole ratios of lactide:glycolide:caprolactone that can be the same or different from one another. For the first (elastomeric) poly(D,L-lactide-co-glycolide-co-ϵ-caprolactone), D,L-lactide can be present in a mol % ranging from 10 to 60%, glycolide can be present in a mol % ranging from 10 to 60%, and ϵ-caprolactone can be present in a mol % ranging from 10 to 80%. For the second (tacky) poly(D,L-lactide-co-glycolide-co-ϵ-caprolactone), D,L-lactide can be present in a mol % ranging from 10 to 60%, glycolide can be present in a mol % ranging from 10 to 50%, and ϵ-caprolactone can be present in a mol % ranging from 10 to 80%. Tables 1 and 2 list mol % compositions for the first (elastomeric) and second (tacky) poly(D,L-lactide-co-glycolide-co-ϵ-caprolactone)s.

TABLE 1 mol % compositions for first (elastomeric) poly(D,L-lactide-co-glycolide-co-ϵ-caprolactone).

| D,L-lactide mol % | Glycolide mol % | ϵ-caprolactone mol % |
|---|---|---|
| 10 | 10 | 80 |
| 20 | 10 | 70 |
| 30 | 10 | 60 |
| 40 | 10 | 50 |
| 50 | 10 | 40 |
| 60 | 10 | 30 |
| 10 | 20 | 70 |
| 20 | 20 | 60 |
| 30 | 20 | 50 |
| 40 | 20 | 40 |
| 50 | 20 | 30 |
| 60 | 20 | 20 |
| 10 | 30 | 60 |
| 20 | 30 | 50 |
| 30 | 30 | 40 |
| 40 | 30 | 30 |
| 50 | 30 | 20 |
| 60 | 30 | 10 |
| 10 | 40 | 50 |
| 20 | 40 | 40 |
| 30 | 40 | 30 |
| 40 | 40 | 20 |
| 50 | 40 | 10 |
| 10 | 50 | 40 |
| 20 | 50 | 30 |
| 30 | 50 | 20 |
| 40 | 50 | 10 |
| 10 | 60 | 30 |
| 20 | 60 | 20 |

TABLE 2 mol % compositions for second (tacky) poly(D,L-lactide-co-glycolide-co-ε-caprolactone).

| D,L-lactide mol % | Glycolide mol % | ε-caprolactone mol % |
|---|---|---|
| 10 | 10 | 80 |
| 20 | 10 | 70 |
| 30 | 10 | 60 |
| 40 | 10 | 50 |
| 50 | 10 | 40 |
| 60 | 10 | 30 |
| 10 | 20 | 70 |
| 20 | 20 | 60 |
| 30 | 20 | 50 |
| 40 | 20 | 40 |
| 50 | 20 | 30 |
| 60 | 20 | 20 |
| 10 | 30 | 60 |
| 20 | 30 | 50 |
| 30 | 30 | 40 |
| 40 | 30 | 30 |
| 50 | 30 | 20 |
| 10 | 40 | 50 |
| 20 | 40 | 40 |
| 30 | 40 | 30 |
| 40 | 40 | 20 |
| 50 | 40 | 10 |
| 10 | 50 | 40 |
| 20 | 50 | 30 |
| 30 | 50 | 20 |

The amount and exact composition of the blend can be altered to maximize compatibility with a substrate of an implant device. For example, the monomer composition of the second (tacky) polymer can be tailored to be more hydrophilic in order to maximize adhesion to a hydrophilic substrate such as titanium or titanium oxide. A more hydrophobic second (tacky) polymer may be used to adhere to a less polar substrate such as parylene or a biodegradable drug eluting strip, such as a strip made from the lactide/glycolide family of biodegradable polymers.

The blends can further comprise other additives. Other additives that can be used to tune the physical properties of the blend include humectants such as glycerin or PEG, and plasticizers such as unreacted monomer, i.e. lactide, glycolide, or ε-caprolactone, as well as mineral oil or lanolin.

The blends can be prepared by mixing the first and second polymers (and any other additives or components) together in a commercial blender, such as a PATTERSON-KELLY blender, under high shear conditions. The blends can also be prepared by reactive extrusion, extrusion mixing, mixing at low shear with the aid of heat, or dry admixing, in addition to high shear blending.

Each terpolymer can be prepared by copolymerizing (ring-opening polymerizing) D,L-lactide, glycolide, and ε-caprolactone in a desired molar ratio using a suitable initiator. A variety of nucleophilic initiators can be used. The initiator can be PEG, PPO, PEG/PPO copolymers, fatty alcohols or polyalcoholic species such as glycerin, and saccharides as well as water and glycolic acid or 1-dodecanol. Catalysts may also be used during polymerization, such as stannous octoate. The polymerization can proceed from 8 to 24 hours at from 130° C. to 180° C., after which time any unreacted monomer can be removed under vacuum. A poly(D,L-lactide-co-glycolide-co-ε-caprolactone) of a particular molecular weight can be prepared by using the appropriate amounts of initiator relative to monomer feed, which can control the length of the polymer chains produced.

In one aspect, the first poly(D,L-lactide-co-glycolide-co-ε-caprolactone) can be cross-linked with a molecule having 2 or more hydroxyl groups to increase the polymer's cohesive strength using methods known in the art.

Cohesiveness of the first (elastomeric) polymer may also be improved by sequential copolymerization using an alcohol initiator, e.g. hexanediol, of caprolactone, glycolide, and lactide. L-lactide can also be polymerized with caprolactone and glycolide in the solid-state using polyethylene glycol (PEG), polypropylene oxide (PPO), or PEG/PPO macroinitiators.

The poly(D,L-lactide-co-glycolide-co-ε-caprolactone) blends can be sterilized prior to use, preferably using γ-ray irradiation at a dosage of about 25 kGy. The irradiation procedure can reduce the molecular weights of the polymers in the blend. One can thus start with terpolymers having a slightly higher (about 10,000 Daltons higher) molecular weight than the final targeted molecular weight of each terpolymer in the blend.

In another aspect, the blend comprises (a) a poly(D,L-lactide-co-glycolide-co-ε-caprolactone) having a molecular weight of from 75,000 to 250,000 Daltons and a polydispersity index (PDI) of less than 2.0, and (b) a poly(D,L-lactide-co-glycolide-co-mPEG) having a molecular weight of 25,000 or less and a polydispersity index (PDI) of less than 2.0; wherein the poly(D,L-lactide-co-glycolide-co-mPEG) has a molecular weight ($M_w$) that can be less than the poly(D,L-lactide-co-glycolide-co-ε-caprolactone); and wherein the weight ratio of the poly(D,L-lactide-co-glycolide-co-ε-caprolactone) to the poly(D,L-lactide-co-glycolide-co-mPEG) can be from about 95:5 to about 75:25.

For this blend, the poly(D,L-lactide-co-glycolide-co-ε-caprolactone) is described above as the first (elastomeric) polymer. The poly(D,L-lactide-co-glycolide-co-mPEG) can be the tacky component of the blend. The poly(D,L-lactide-co-glycolide-co-mPEG) has a molecular weight ($M_w$) of 25,000 or less, or from 10,000 to 20,000 Daltons. The poly(D,L-lactide-co-glycolide-co-mPEG) has a polydispersity index (PDI) of less than 2.0, or from 1.4 to 1.7. The poly(D,L-lactide-co-glycolide-co-mPEG) has a glass transition temperature ($T_g$) of 0° C. or less, such as from about −20° C. to about 0° C. For example, the poly(D,L-lactide-co-glycolide-co-mPEG) can have a glass transition temperature ($T_g$) of 0, −5, −8, −9, −10, −12, −15, or −20° C.

The weight ratio of the poly(D,L-lactide-co-glycolide-co-ε-caprolactone) to the poly(D,L-lactide-co-glycolide-co-mPEG) can range from about 95:5 to about 70:30, for example, 95:5, 90:10, 80:20, or 70:30.

The molar ratio of D,L-lactide to glycolide in the poly(D,L-lactide-co-glycolide-co-ε-caprolactone) can range from 90:10 to 40:60, for example, 90:10, 80:20, 70:30, 60:40, 50:50, or 40:60. The polyethylene glycol (mPEG) portion exists as a block on the end of a poly(D,L-lactide-co-glycolide) chain. Such a poly(D,L-lactide-co-glycolide-co-ε-caprolactone) is prepared by initiating D,L-lactide and glycolide with an mPEG initiator. Thus, the mPEG portion of the polymer can be defined by the starting mPEG initiator, in terms of molecular weight ($M_w$). The PEG initiators can be obtained commercially, and the molecular weight ($M_w$) of the PEG refers to the molecular weight listed by the commercial supplier. A specific example is mPEG 2000, which has a molecular weight ($M_w$) of about 2000 as listed by the commercial supplier Spectrum Chemicals and Laboratory Products, New Brunswick, N.J.

The poly(D,L-lactide-co-glycolide-co-mPEG) can also be characterized by the molar ratio of lactide, glycolide, and ethylene glycol in the polymer. The lactide mol % can range from 10 to 60%, the glycolide mol % can range from 10 to 60%, and the ethylene glycol can range from 10 to 80%. Table 3 lists mol % compositions for the poly(D,L-lactide-co-glycolide-co-mPEG) component.

TABLE 3 mol % compositions for poly(D,L-lactide-co-glycolide-co-mPEG).

| D,L-lactide mol % | Glycolide mol % | Ethylene glycol mol % |
| --- | --- | --- |
| 10 | 10 | 80 |
| 20 | 10 | 70 |
| 30 | 10 | 60 |
| 40 | 10 | 50 |
| 50 | 10 | 40 |
| 60 | 10 | 30 |
| 10 | 20 | 70 |
| 20 | 20 | 60 |
| 30 | 20 | 50 |
| 40 | 20 | 40 |
| 50 | 20 | 30 |
| 60 | 20 | 20 |
| 10 | 30 | 60 |
| 20 | 30 | 50 |
| 30 | 30 | 40 |
| 40 | 30 | 30 |
| 50 | 30 | 20 |
| 10 | 40 | 50 |
| 20 | 40 | 40 |
| 30 | 40 | 30 |
| 40 | 40 | 20 |
| 50 | 40 | 10 |
| 10 | 50 | 40 |
| 20 | 50 | 30 |
| 30 | 50 | 20 |

Alternatively, the poly(D,L-lactide-co-glycolide-co-mPEG) can be characterized by its molar percentages and lactide and glycolide and by the molecular weight of the mPEG block. In certain aspects, the polymer can comprise from 50 mol % DL-lactide to 100 mol % DL-lactide and less than or equal to 50 mol % glycolide for a family of mPEG-based terpolymers wherein the $M_w$ of the mPEG portion ranges from about 350 to 5000 Daltons (based on the molecular weight of the starting mPEG initiator).

The poly(D,L-lactide-co-glycolide-co-mPEG) can be made using the methods discussed above. D,L-lactide and glycolide are copolymerized using a mPEG initiator which has nucleophilic end groups. mPEGs are commercially available with alcohol endgroups, which can initiate the ring-opening polymerization of D,L-lactide and glycolide. The polymerization can be carried out in the presence of a catalyst as discussed above.

The article comprises a pressure-sensitive adhesive (PSA) having a first adhesive surface and an opposing second adhesive surface, the pressure-sensitive adhesive (PSA) comprising any of the blends disclosed above; and a release liner having a surface thereof adhered to the first adhesive surface of the pressure-sensitive adhesive.

The article can have any desired shape. For example, the article can be substantially spherical, cylindrical, planar, or cubical. A planar article can be substantially square, rectangular, circular, triangular, among other shapes. In one aspect, the article can be square or rectangular. In a further aspect, the article has a shape that can be non-rectangular. As shown in FIG. 1, the article 100 comprises the pressure-sensitive adhesive having a second adhesive surface 110 opposing a surface of the release liner 130. The first adhesive surface 120 of the pressure-sensitive adhesive can be adhered to the surface of the release liner 130 and can be removed by peeling the pressure-sensitive adhesive away from the surface of the release liner 130. The pressure-sensitive adhesive can optionally comprise a bioactive agent (not shown) dispersed therein. Prior to the pressure-sensitive adhesive being used, the adhesive can be at least partially, or fully, covered with the release liner.

The articles can have any desired size. When the pressure-sensitive adhesive comprises a bioactive agent, the size selection of the article can be influenced by the desired loading of the bioactive agent. Generally, the more bioactive agent that is desired, the larger the article will be. The size can also be selected so as to provide the desired release properties of the pressure-sensitive adhesive film. In addition, when the pressure-sensitive adhesive is applied to an implant device, the size of the implant device can be of importance when selecting the size of the article. For example, it can be desirable for portions of the implant device surface to remain exposed. In these instances, the size of the pressure-sensitive adhesive can be selected so as to not completely cover the implant device surface.

The pressure-sensitive adhesive can have any desired thickness. In one aspect, the pressure-sensitive adhesive can be a thin film having a thickness of from about 1 nm, or less, to about 1000 nm, including without limitation those films having thicknesses of about 5 nm, 20 nm, 50 nm, 150 nm, 200 nm, 300 nm, 500 nm, 800 nm, or 900 nm. In a further aspect, the film has a thickness greater than about 1000 nm, including without limitation those films having thicknesses of from about 1000 nm to about 50 microns, or greater. For example, the film can have a thickness of about 2000 nm, 0.1 cm, 0.5 cm, 1 cm, 5 cm, 20 cm, 30 cm, 40 cm, or 50 cm. It is to be understood that the film does not have to be, but can be, planar. Thus, in various aspects, the film may have varying heights at different regions of the film. As such, the film can comprise any shape, as discussed above, depending on the desired shape of the article.

Figure 2:
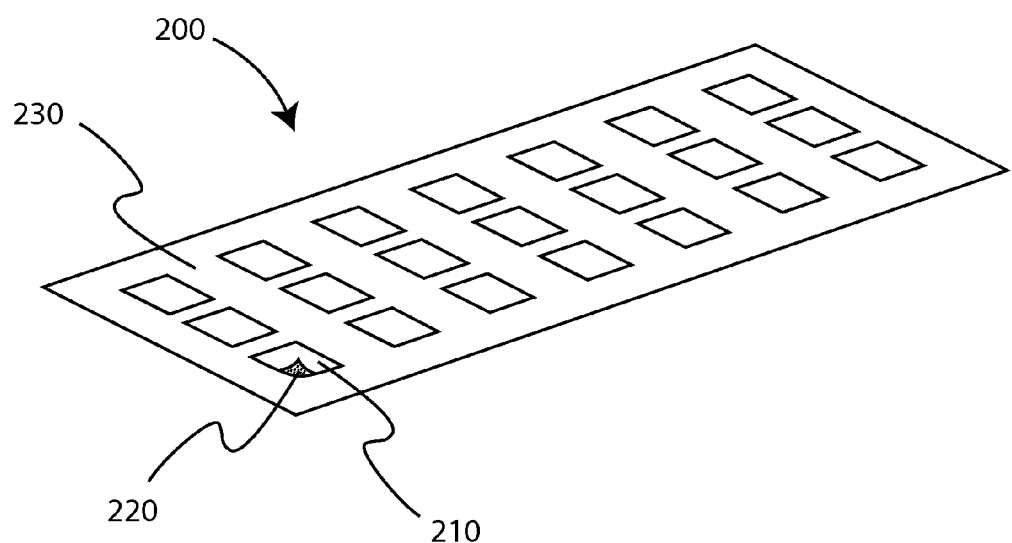
FIG. 2 is a drawing of an article comprising multiple pressure-sensitive adhesive blends adhered to a single release liner.

The article can also be comprised of a plurality of pressure-sensitive adhesives adhered to a single release liner. Such an article, for example, is shown in FIG. 2 (200), which shows a planar release liner 230 comprising a plurality of pressure-sensitive adhesives adhered thereto. As shown, the article comprises a plurality of pressure-sensitive adhesives 210 having at least an adhesive surface 220 that is adhered to a surface of the release liner. In this example, the article comprises a plurality of pressure-sensitive adhesives that all share the same release liner 230. However, alternate embodiments include kits that are a package of a plurality of articles, such as those depicted in FIG. 1. A kit of articles can also comprise a mixture of the same or different articles. For example, the kit can comprise several sets of articles, each having a different size. Such a kit may be useful for point of use applications of the articles, wherein one kit, for example, can provide articles that are compatible in size with a number of different implant devices.

Any suitable release liner can be used. The release liner can be a temporary release liner that is removed from the pressure-sensitive adhesive of the article prior to the article being implanted into a subject or prior to being applied to an implant device. As such, a temporary release liner that does not leave behind any material in a quantity that could be harmful to a subject can be used.

Suitable release liners are those that are made of materials that permit the release liner to be easily stripped or peeled away from the adjacent pressure-sensitive adhesive. Exemplary release liners are those that are comprised of paper and/or a plastic material. Typically, such release liners are made from polymers such as polyesters or polyethylenes which are coated with materials such as silicone or fluorinated hydrocarbons that reduce the adhesiveness between the release liner and the adjacent adhesive. Other suitable release liners include paper, such as kraft paper, that can be covered with a silicone material, which permits the easy release of the liner from the adhesive. Release liner materials are available commercially, for example, coated polyethylene liners are commercially available from 3M®.

In one aspect, the release liner can be the polymer film, or the polymer film can be packed as a roll of tape comprising a middle backing layer in between a release liner layer and a pressure-sensitive adhesive layer, or another suitable configuration. That is, the surface of the pressure-sensitive adhesive can be adhered to an opposing second surface of the polymer film with an adhesive or a release liner backing layer. For example, the article can be configured as a roll of tape, wherein the surface of the pressure-sensitive adhesive functions as the release liner. In other aspects, such as those discussed above, the release liner is not the polymer film but rather a distinct layer.

The implant device comprises a substrate having a disclosed blend adhered to a surface thereof. The blend allows the implant device to be secured to a particular location within a subject. As discussed below, a surface of the implant device can also comprise a bioactive layer separate from the blend layer, which can be useful for delivering a bioactive agent a particular location in a subject.

The implant device can comprise any shape, such as a rod, a fiber, a cylinder, a bead, a ribbon, a disc, a wafer, a free-formed shaped solid, or a variety of other shaped solids. The device can have any regular or irregular shape and can have any cross section like circular, rectangular, triangular, oval, and the like. In one aspect, the device comprises a cylindrical disk-shape, such as a typical shape of an implantable pump.

The implant can be comprised of any suitable material, such as a metal (e.g., titanium), metal composite, organic material, polymeric, biodegradable, or even ceramic material. The surface of the implant can be any shaped surface, and may have a porous, beaded or meshed ingrowth surface, as can be present in certain implants.

The implant device can be any type of medical implant. The implant devices can include, for example, implants for drug delivery, including drug delivery pumps; orthopedic implants, including spinal implants, implants for osseointegration or bone repair; medical stents, including stents with inherent drug delivery capability; prosthetic implants, including breast implants, muscle implants, and the like; dental implants; ear implants, including cochlear implants and hearing devices; cardiac implants including pacemakers, catheters, etc.; space filling implants; bioelectric implants; neural implants; internal organ implants, including dialysis grafts; defribrillators; monitoring devices; recording devices; stimulators, including deep brain stimulators, nerve stimulators, bladder stimulators, and diaphragm stimulators; implantable identification devices and information chips; artificial organs; drug administering devices; implantable sensors/biosensors; screws; tubes; rods; plates; or artificial joints.

Other implant devices that may benefit when used with the disclosed compositions include those with one or more active surfaces, e.g., a surface that enhances a connection between a tissue or fluid and the implant device, or a surface that allows for or enhances wound healing. The disclosed pressure-sensitive adhesives can be effective when applied to only a portion of the implant device, allowing for any active surface to remain exposed and functional when the implant device is implanted in a subject.

Figure 3:
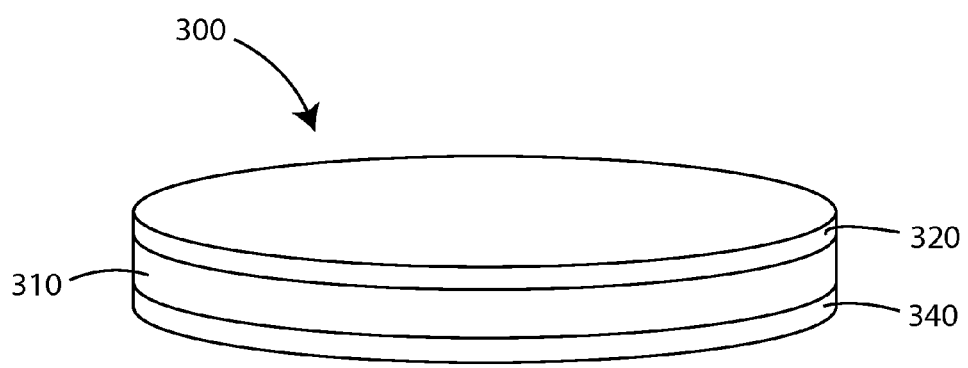
FIG. 3 is an isometric view of a biodegradable disc-shaped implant device comprising a bioactive layer and a pressure-sensitive adhesive (PSA) blend layer.

An exemplary implant device 300 is shown in FIG. 3. The implant device 300 comprises a disk-shaped substrate 310 having a first planar surface (not shown), and a second planar surface (not shown) parallel to the first planar surface, and an annular edge surface contiguous with the first and second planar surfaces. The blend 320 is adhered to the first planar surface. The exemplary implant device 300 a bioactive layer 340 adhered to the second planar surface of the substrate. The bioactive layer 340 comprises a bioactive agent dispersed within a biodegradable polymer matrix, such as a poly(D,L-lactide-co-glycolide) having a molecular weight of 20,000 Daltons or less.

Typically, before applying the composition and/or coating to the implant device, the implant device surface can be cleaned or treated to remove any surface contaminants and to promote good adhesion of the blend and/or bioactive layer. For example, the implant device can be sterilized. The implant device can then be implanted into the subject using known surgical techniques. In certain aspects, it can be desirable to store the blends and articles in a sterilized container or package prior to use.

The implant device can be implanted in any desired subject. The subject can be a vertebrate, such as a mammal, a fish, a bird, a reptile, or an amphibian. The subject of the herein disclosed methods can be, for example, a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered.

The bioactive agent can be present in the bioactive layer and/or the blend layer in any suitable amount. For example, the bioactive agent can be present in an amount ranging from 0.05% to 80% by weight of the implant, for example, 0.1%, 0.5%, 5%, 10%, 15%, 20%, 30%, 40%, 45%, 50%, 55%, 60%, 70%, or 80%.

Examples of bioactive agents that can be incorporated into the bioactive layer and/or blend layer include generally any bioactive agents and particularly, thermally-labile bioactive agents. Examples include without limitation small molecules, peptides, proteins such as hormones, enzymes, antibodies, receptor binding proteins, antibody fragments, antibody conjugates, nucleic acids such as aptamers, iRNA, siRNA, microRNA, DNA, RNA, antisense nucleic acid or the like, antisense nucleic acid analogs or the like, VEGF inhibitors, macrocyclic lactones, dopamine agonists, dopamine antagonists, low-molecular weight compounds, high-molecular-weight compounds, or conjugated bioactive agents.

Other bioactive agents can include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, antipsychotics, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Still other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents include, but are not limited to, peptide drugs, protein drugs, therapeutic antibodies, anticalins, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, anti-inflammatory agents, nonsteroidal anti-inflammatory agents, antiparkinsonian agents, antihypertensive agents, β-adrenergic blocking agents, nutritional agents, anti-TNF agents and the benzophenanthridine alkaloids. The agent can further be a substance capable of acting as a stimulant, sedative, hypnotic, analgesic, anticonvulsant, and the like.

Other bioactive agents include but are not limited to analgesics such as acetaminophen, acetylsalicylic acid, and the like; anesthetics such as lidocaine, xylocalne, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenytoin sodium, diazepam, and the like; antidepressants such as isocarboxazid, amoxapine, and the like; antihistamines such as diphenhydramine HCl, chlorpheniramine maleate, and the like; antipsychotics such as clozapine, haloperidol, carbamazepine, gabapentin, topimarate, bupropion, sertraline, alprazolam, buspirone, risperidone, aripiprazole, olanzapine, quetiapine, ziprasidone, iloperidone, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin B12, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Tinidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

The adhesive blend and the target substrate may possess opposite or distinct surface properties such that a unique primer coating may be useful on the adhesive surface of the blend to maximize adhesion to the substrate or release liner. This can be achieved by spray coating each side of the blend with a primer or tackifier specific to the application and substrate. For example, a low molecular weight tackifier, i.e. low molecular weight terpolymers, can be dissolved in an organic solvent, nebulized and applied to a preformed adhesive matrix.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The following analytical methods were used in all examples, unless indicated otherwise. The inherent viscosity was measured at 0.5% (wt/vol) terpolymer in chloroform at 30° C. using a Cannon-Fenske size 25 viscometer. Polymer composition was determined from $^1$H-NMR spectra recorded in $CDCl_3$ on a Varian Inova spectrometer at 399.85 MHz. Thermal properties were determined using a TA Instruments Differential Scanning calorimeter (DSC) 2920 with Refrigerated Cooling System (RCS). The thermal history was removed by an initial heat ramp. The glass transition temperature ($T_g$) was determined from the DSC curve obtained from a temperature scan rate of 10° C./minute over a temperature range of about −60° C. to 90° C. Gel permeation chromatography (GPC) analyses were performed on a Perkin Elmer Series 200 GPC/RI fitted with a Waters Styragel HR-2 and two Waters HR-5E columns, using chloroform as the mobile phase, and calibrated with multiple polystyrene standards of narrow molecular weight distribution.

Example 1

Preparation of Elastomeric (first polymer) 30:20:50 DL:G:CL 8A Poly(D,L-lactide-co-glycolide-co-ϵ-caprolactone)

An elastomeric terpolymer poly(D,L-lactide-co-glycolide-co-ϵ-caprolactone) with a D,L-lactide to glycolide to ϵ-caprolactone molar ratio=30:20:50 was made by a ring-opening polymerization process using glycolic acid as the initiator and D,L-lactide, glycolide aid ϵ-caprolactone as the monomer feed. A thoroughly dried resin kettle equipped with a nitrogen inlet, air-cooled distillation adapter with trap, and mechanical stirrer was charged with 261.5 grams (1.814 mol) of DL-lactide (Ortec, South Carolina) and 142.5 grams (1.228 mol) of glycolide (Ortec, South Carolina). The monomer was blanketed with nitrogen and melted at 140° C. 347.2 grams (3.042 mol) of ϵ-caprolactone (Ortec, South Carolina) and 1.393 grams (18.31 mmol) of the initiator glycolic acid (Sigma-Aldrich, Wisconsin) was added. After thorough mixing, the mixture was charged with 223 milligrams (0.550 mmol) of the catalyst stannous octoate (Sigma-Aldrich, Wisconsin). The polymerization proceeded for 18 hours at 170° C. followed by a 2 hour vacuum strip at 28.5 in HG vacuum to remove un-reacted monomer. The final terpolymer was comprised of 30 mol % D,L-lactide, 22 mol % glycolide and 48 mol % ϵ-caprolactone as determined by proton NMR. The polymer had an inherent viscosity (IV) of 0.84 dL/g and a $T_g$ of −12° C. The number and weight average molecular weights were $M_n$=73,000 and $M_w$=119,000, respectively.

Example 2

Preparation of a Tacky (second polymer) 30:20:50 DL:G:CL 6A Poly(D,L-lactide-co-glycolide-co-ϵ-caprolactone)

A terpolymer (302050 DLGCL 6A) was made via the same ring-opening polymerization route described in Example 1 using 174.4 grams (1.210 mol) of DL-lactide (Ortec, South Carolina) and 94.3 grams (0.813 mol) of glycolide (Ortec, South Carolina). The monomer was blanketed with nitrogen and melted at 140° C. 231.7 grams (2.030 mol) of ϵ-caprolactone (Ortec, South Carolina) and 0.933 grams (12.3 mmol) of the initiator glycolic acid (Sigma-Aldrich, Wisconsin) was added. After thorough mixing, the mixture was charged with 147 milligrams (0.364 mmol) of the catalyst stannous octoate (Sigma-Aldrich, Wisconsin). The mole percent of DL-lactide, glycolide and ϵ-caprolactone in the polymer was 29%, 21% and 50%, respectively, The IV was 0.55 dL/g and the Tg −15° C. The number and weight average molecular weights were Mn=39,000 and Mw=65,000.

Example 3

Preparation of a Tacky Poly(D,L-lactide-co-glycolide-co-mPEG)

A terpolymer (5050 DLG mPEG 2K) was made via a ring-opening polymerization using mPEG 2000 as the initiator and DL-lactide and glycolide as the monomer feed similar to that described in Example 1. The polymerization took place in a reactor that was placed in a force-air oven set to 150° C. without mixing. To the reactor was charged 111.9 grams (0.776 mol) of DL-lactide (Ortec, South Carolina), 86.5 grams (0.745 mol) of glycolide (Ortec, South Carolina) and 101.7 grams of dry mPEG 2000 (0.051 mol; Spectrum Chemicals and Laboratory Products, New Brunswick, N.J.) to which 0.150 grams (0.370 mmol) of the catalyst stannous octoate (Sigma-Aldrich, Wisconsin) was added. The mole percent of DL-lactide, glycolide and ethylene glycol in the polymer was 20%, 20% and 60%, respectively. The IV was 0.19 dL/g and the Tg=−9° C. The number and weight average molecular weights were $M_n$=10,000 and $M_w$=14,000.

Example 4

Implant Device

Implant devices were prepared by adhering a thin solvent-cast adhesive film from dichloromethane onto a ~1 mm backing element (substrate) made from poly(lactide-co-caprolactone), i.e. the material described in Example 5. PSA formulations were made by dissolving the appropriate terpolymer blends in dichloromethane (~15% w/w) at ambient temperature for at least 12 hours. Polymer films were cast onto sheets of Teflon (release liner), and the solvent was allowed to evaporate under a stream of nitrogen gas or vacuum. Finished devices were prepared by applying a ~1 inch disk of flexible substrate material onto the sheet of pressure-sensitive adhesive film still adhered to the Teflon release liner, and with the aid of a scalpel, each device was cut and trimmed in the form of a circular 1" laminated device. The adhesive/cohesive properties of a device were qualitatively assessed by a 90 degree peel test. The pressure-sensitive adhesive blend was affixed to a titanium substrate with an applied pressure of 3 to 5 PSI for 10 seconds followed by a 1 minute equilibration time at ambient temperature. Adhesion was graded by the amount of force that was required to remove the PSA device from the metal substrate and cohesion was graded by visually examining the amount of adhesive material remaining adhered to the metal substrate after the device was peeled.

A variety of implant devices comprising a layer of a PSA blend were prepared. In one example, the PSA was a blend of the materials described in Examples 1 and 3 comprising 90 mol % of 302050 DLGCL 8A and 10 mol % 5050 DLG mPEG 2K. The PSA blend exhibited excellent adhesive and cohesive properties as it stuck reversibly to a titanium surface with the application of pressure and could be peeled with minimal loss of adhesive to the metal surface. PSA blends and devices were also formulated from the terpolymers described in the Examples 1 and 2. Binary adhesive blends 302050 DLGCL 8A and 302050 DLGCL 6A terpolymers at 85/15 and 70/30 weight ratios, respectively, exhibited excellent adhesive and cohesive properties. The adhesive/cohesive balance can be modified by altering the monomer composition as well as the molar ratio of each terpolymer in the blend.

Example 5

Preparation of Biodegradable Substrate of Implant Device

A biodegradable substrate comprising poly(L-lactide-co-ε-caprolactone) was prepared as follows. A high pressure pipe (316 stainless steel) was charged with 154.9 grams (1.075 mol) of L-lactide and 45.7 grams (0.400 mol) of ε-caprolactone, blanketed with nitrogen, sealed and heated to 140° C. in a forced-air oven. After the monomer melted, 1.20 grams (6.44 mmol) of 1-dodecanol and 101 milligrams (0.249 mmol) of the catalyst stannous octoate were added. The tube was purged with nitrogen, sealed and shaken vigorously by hand to insure good mixing. The polymerization proceeded for 18 hours at 170° C. The resulting polymer was extruded into the shape of a disc and flattened with a Teflon rod, cooled under vacuum (28.5 inches Hg vacuum), and stored at 4° C. until further use.

The polymer of the substrate was found to have the following properties. The L-lactide:ε-caprolactone mole ratio was 72:28. The polymer composition comprised residual L-lactide in an amount of 3.4 wt % and residual ε-caprolactone in an amount of 0.6 wt %. The polymer had an intrinsic viscosity (IV)=1.47 dL/g, $T_g$=21.8° C., $M_w$=238,000, $M_n$=125,000, and polydispersity index (PDI)=1.9.

Example 7

Bioactive Layer of Implant Device

Poly(D,L-lactide-co-glycolide) Synthesis.

A resin kettle under a nitrogen blanket was charged with 605.2 grams (4.199 mol) of D,L-lactide and 146.0 grams (1.258 mol) of glycolide and was heated to 140° C. 1-dodecanol (42.28 grams; 226.9 mmol) and 240 milligrams (0.592 mmol) of the catalyst stannous octoate was subsequently added. The polymerization was allowed to proceed for 4 hours at 170° C. followed by a 2 hour vacuum strip at 28.5 inches of Hg vacuum to remove un-reacted monomer. The resulting polymer was poured into a Teflon lined tray filled with liquid nitrogen and stored at 4° C. The polymer was cryo-milled with a bench top Stephan Mill and stored at 4° C.

The resulting polymer was found to have the following properties. The D,L-lactide:glycolide mole ratio was 76:24. The composition comprised residual D,L-lactide in an amount of 2.1 wt. %, and residual glycolide in an amount of 0.1 wt. %. The polymer had an intrinsic viscosity (IV)=0.14 dL/g, $T_g$=25.4° C., $M_w$=11,000, $M_n$=6,000, and polydispersity index (PDI=1.8).

Poly(D,L-lactide-co-glycolide), Bioactive Agent Formulation.

A formulation of bioactive agent and the poly(D,L-lactide-co-glycolide) discussed above was prepared. The poly(D,L-lactide-co-glycolide) and bioactive agents Minocycline and Rifampin were added to a mixed solvent system of Acetone (68% w/w) and Methanol (32%, w/w) to provide a composition having 68% poly(D,L-lactide-co-glycolide), 12% Minocycline, and 20% Rifamcin (all % by weight). The overall solids concentration was 300 mg/mL (36 mg/mL Minocycline, 60 mg/mL Rifampin, and 204 mg/mL poly(D,L-lactide-co-glycolide).

Applying Bioactive Layer to Implant Device.

The bioactive formulation discussed above was deployed onto the substrate discussed in Example 6. The coating operation was performed at ambient temperature (68-74° F.) in an enclosed humidity-controlled coating chamber using an ultrasonic sprayhead, which atomizes the coating solution and deposits it on the substrate. A syringe pump was used to deliver the coating composition to the sprayhead. The bioactive layer coated implant device was dried under nitrogen for a minimum of 16 hours. All other operations (pre and post coating) were performed at ambient conditions (30 to 40% relative humidity). The coated substrates (implant devices) were stored at −20° C. until further use.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. An article, comprising:
a pressure-sensitive adhesive (PSA) having a first adhesive surface and an opposing second adhesive surface, the pressure-sensitive adhesive (PSA) comprising (A) the blend comprising:
(a) a first poly(D,L-lactide-co-glycolide-co-ε-caprolactone) having a molecular weight ($M_w$) of from 75,000 to 250,000 Daltons and a polydispersity index (PDI) of less than 2.0, and
(b) a second poly(D,L-lactide-co-glycolide-co-e-caprolactone) having a molecular weight ($M_w$) of 60,000 to 130,000 Daltons and a polydispersity index (PDI) of less than 2.0;
wherein the second poly(D,L-lactide-co-glycolide-co-e-caprolactone) has a molecular weight ($M_w$) that is less than the first poly(D,L-lactide-co-glycolide-co-ε-caprolactone); and
wherein the weight ratio of the first poly(D,L-lactide-co-glycolide-co-ε-caprolactone) to the second poly(D,L-lactide-co-glycolide-co-e-caprolactone) is from about 90:10 to about 60:40, or
(B) the blend comprising:
(a) a third poly(D,L-lactide-co-glycolide-co-ε-caprolactone) having a molecular weight of from 75,000 to 250,000 Daltons and a polydispersity index (PDI) of less than 2.0, and
(b) a poly(D,L-lactide-co-glycolide-co-mPEG) having a molecular weight of less than 25,000 Daltons and a polydispersity index (PDI) of less than 2.0; and
wherein the weight ratio of the poly(D,L-lactide-co-glycolide-co-ε-caprolactone) to the poly(D,L-lactide-co-glycolide-co-mPEG) is from about 95:5 to about 75:25; and
a release liner having a surface thereof adhered to the first adhesive surface of the pressure-sensitive adhesive.

2. The article of claim 1, wherein the weight ratio of the first poly(D,L-lactide-co-glycolide-co-c-caprolactone) to the second poly(D,L-lactide-co-glycolide-co-e-caprolactone) is from about 85:15 to about 70:30.

3. The article of claim 1, wherein the first poly(D,L-lactide-co-glycolide-co-e-caprolactone) has a molecular weight ($M_w$) of from 100,000 to 130,000 Daltons.

4. The article of claim 1, wherein the first poly(D,L-lactide-co-glycolide-co-e-caprolactone) has a polydispersity index (PDI) ranging from 1.5 to 1.8.

5. The article of claim 1, wherein the second poly(D,L-lactide-co-glycolide-co-e-caprolactone) has a polydispersity index (PDI) ranging from 1.5 to 1.8.

6. The article of claim 1 wherein the weight ratio of the third poly(D,L-lactide-co-glycolide-co-ε-caprolactone) to the poly(D,L-lactide-co-glycolide-co-mPEG) is from about 90:10 to about 85:15.

7. The article of claim 1, wherein the third poly(D,L-lactide-co-glycolide-co-e-caprolactone) has a molecular weight ($M_w$) of from 100,000 to 130,000 Daltons.

8. The article of claim 1, wherein the poly(D,L-lactide-co-glycolide-co-mPEG) has a molecular weight ($M_w$) of from 10,000 to 20,000 Daltons.

9. The article of claim 1, wherein the third poly(D,L-lactide-co-glycolide-co-e-caprolactone) has a polydispersity index (PDI) ranging from 1.5 to 1.8.

10. The article of claim 1, wherein the poly(D,L-lactide-co-glycolide-co-mPEG) has a polydispersity index (PDI) ranging from 1.4 to 1.7.

11. An implant device comprising
a substrate
a planar layer of a pressure-sensitive adhesive (PSA) adhered to a surface of the substrate, the PSA comprising a blend,
(A) the blend comprising:
(a) a first poly(D,L-lactide-co-glycolide-co-ε-caprolactone) having a molecular weight ($M_w$) of from 75,000 to 250,000 Daltons and a polydispersity index (PDI) of less than 2.0, and
(b) a second poly(D,L-lactide-co-glycolide-co-e-caprolactone) having a molecular weight ($M_w$) of 60,000 to 130,000 Daltons or less and a polydispersity index (PDI) of less than 2.0;
wherein the second poly(D,L-lactide-co-glycolide-co-e-caprolactone) has a molecular weight ($M_w$) that is less than the first poly(D,L-lactide-co-glycolide-co-ε-caprolactone); and
wherein the weight ratio of the first poly(D,L-lactide-co-glycolide-co-ε-caprolactone) to the second poly(D,L-lactide-co-glycolide-co-e-caprolactone) is from about 90:10 to about 60:40, or
(B) the blend comprising:
(a) a poly(D,L-lactide-co-glycolide-co-ε-caprolactone) having a molecular weight of from 75,000 to 250,000 Daltons and a polydispersity index (PDI) of less than 2.0, and
(b) a poly(D,L-lactide-co-glycolide-co-mPEG) having a molecular weight of less than 25,000 Daltons and a polydispersity index (PDI) of less than 2.0; and
wherein the weight ratio of the poly(D,L-lactide-co-glycolide-co-ε-caprolactone) to the poly(D,L-lactide-co-glycolide-co-mPEG) is from about 95:5 to about 75:25.

12. The implant device of claim 11, the blend forming a layer wherein the substrate further comprises a bioactive layer adhered to a surface of the blend layer, the bioactive layer comprising a bioactive agent dispersed within a poly(D,L-lactide-co-glycolide) having a molecular weight of 20,000 Daltons or less.

13. The implant device of claim 11, wherein the substrate is flexible.

14. The implant device of claim 11, wherein the substrate is biodegradable.

15. The implant device of claim 11, wherein the substrate comprises poly(L-lactide-co-ε-caprolactone).

16. The implant device of claim 11, wherein the substrate comprises titanium or stainless steel.

17. The implant device of claim 11, wherein the substrate has a first surface and an opposing second surface and wherein the blend is disposed on the first surface.

18. The implant device of claim 17, wherein the substrate is a disk-shaped substrate.

19. The implant device of claim 17, wherein the first and second surfaces are planar.

20. The implant device of claim 17, wherein the second surface is parallel to the first surface.

21. The implant device of claim 17, further comprising an annular edge surface contiguous with the first and second surfaces.

22. The implant device of claim 17, further comprising a bioactive layer comprising a bioactive agent dispersed within a poly(D,L-lactide-co-glycolide) having a molecular weight of 20,000 Daltons or less, wherein the bioactive layer is adhered to the second surface.

* * * * *

UNITED STATES PATENT AND TRADEMARK OFFICE
CERTIFICATE OF CORRECTION

PATENT NO. : 8,920,921 B2  
APPLICATION NO. : 13/221415  
DATED : December 30, 2014  
INVENTOR(S) : Howard Bowman and Bruce W. Hudson It is certified that error appears in the above-identified patent and that said Letters Patent is hereby corrected as shown below:

Title page

Item (73) Assignee: "SURMODICS" should read -- SURMONICS --.

Claims

Claim 2, Column 17, Line 33, "(D,L-lactide-co-glycolide-co-c-caprolactone)" should read -- (D,L-lactide-co-glycolide-co-ε-caprolactone) --.

Claim 11, Column 18, Line 13, Delete "or less".

Signed and Sealed this  
Eighth Day of September, 2015

Michelle K. Lee  
*Director of the United States Patent and Trademark Office*